(12) United States Patent
Sano et al.

(10) Patent No.: US 12,364,425 B2
(45) Date of Patent: Jul. 22, 2025

(54) STORAGE CASE WITH BIOMEDICAL ELECTRODE PAD, AND BIOLOGICAL SIGNAL PROCESSING DEVICE INCLUDING STORAGE CASE WITH BIOMEDICAL ELECTRODE PAD

(71) Applicants: NIPRO CORPORATION, Osaka (JP); HARADA ELECTRONICS CO., LTD., Sapporo (JP)

(72) Inventors: Yoshihiko Sano, Osaka (JP); Masahide Harada, Sapporo (JP)

(73) Assignees: NIPRO CORPORATION, Osaka (JP); HARADA ELECTRONICS CO., LTD., Sapporo (JP)

( * ) Notice: Subject to any disclaimer, the term of this patent is extended or adjusted under 35 U.S.C. 154(b) by 754 days.

(21) Appl. No.: 17/623,156

(22) PCT Filed: Jun. 23, 2020

(86) PCT No.: PCT/JP2020/024659
§ 371 (c)(1),
(2) Date: Dec. 27, 2021

(87) PCT Pub. No.: WO2020/262403
PCT Pub. Date: Dec. 30, 2020

(65) Prior Publication Data
US 2022/0265192 A1     Aug. 25, 2022

(30) Foreign Application Priority Data

Jun. 27, 2019   (JP) ................................ 2019-120222

(51) Int. Cl.
*A61B 5/282*   (2021.01)
*A61B 5/00*   (2006.01)
(Continued)

(52) U.S. Cl.
CPC ............ *A61B 5/282* (2021.01); *A61B 5/0024* (2013.01); *A61B 5/6833* (2013.01); *A61B 50/00* (2016.02);
(Continued)

(58) Field of Classification Search
CPC ..... A61B 5/282; A61B 5/0024; A61B 5/6833; A61B 50/00; A61B 2050/00; A61B 2560/00
See application file for complete search history.

(56) References Cited

U.S. PATENT DOCUMENTS

2008/0139953 A1*   6/2008   Baker ................... A61B 5/024
                                                        600/509
2012/0088999 A1*   4/2012   Bishay .................. A61B 5/332
                                                        600/382
(Continued)

FOREIGN PATENT DOCUMENTS

CN      107949324 A     4/2018
EP      3 777 670 A1    2/2021
(Continued)

OTHER PUBLICATIONS

Jun. 30, 2023 Extended European Search Report issued in European Patent Application No. 20833180.1.
(Continued)

*Primary Examiner* — Joseph A Stoklosa
*Assistant Examiner* — Annie L Shoulders
(74) *Attorney, Agent, or Firm* — Oliff PLC

(57) ABSTRACT

A storage case with a biomedical electrode pad for storing a biological signal processing circuit unit for processing an biological electrical signal which has been detected by the biomedical electrode pad, wherein a case body thereof has a storage area for the biological signal processing circuit unit, the storage area being provided in an openable and
(Continued)

closable manner, and the biological signal processing circuit unit is detachable with respect to the storage area.

6 Claims, 9 Drawing Sheets

(51) Int. Cl.
*A61B 50/00* (2016.01)
*A61B 50/30* (2016.01)

(52) U.S. Cl.
CPC . *A61B 2050/005* (2016.02); *A61B 2050/3014* (2016.02); *A61B 2560/0406* (2013.01)

(56) References Cited

U.S. PATENT DOCUMENTS

| | | | |
|---|---|---|---|
| 2014/0206977 A1 | 7/2014 | Bahney et al. | |
| 2016/0045135 A1* | 2/2016 | Kim | A61B 5/4812 600/391 |
| 2018/0235501 A1* | 8/2018 | Nishimura | H01R 13/6581 |
| 2020/0128670 A1* | 4/2020 | Chong Rodriguez | A61B 5/329 |
| 2021/0007623 A1 | 1/2021 | Sano et al. | |

FOREIGN PATENT DOCUMENTS

| | | |
|---|---|---|
| JP | 2016-504159 A | 2/2016 |
| JP | 2019-037693 A | 3/2019 |
| WO | 2017/043595 A1 | 3/2017 |

OTHER PUBLICATIONS

Jul. 16, 2024 Office Action issued in Japanese Patent Application No. 2021-527656.

Sep. 19, 2023 Office Action issued in Chinese Patent Application No. 202080046219.9.

Feb. 27, 2024 Office Action Issued in Japanese Patent Application No. 2021-527656.

"Holter Electrocardiography Equipment Connection Guide," Holter Electrocardiography-Relaled Products, p. 61, Fukuda Denshi Co., Ltd., Retrieved Feb. 15, 2018, URL: <http://www.fukuda.co.jp/medical/products/holter_ecg/pdf/holter_ecg.pdf>.

"Lead, Relay, and Electrode Cords for Holter Electrocardiography," Holter Electrocardiography-Related Products, p. 65, Fukuda Denshi Co., Ltd., Retrieved Feb. 15, 2018, URL: [<http://www.fukuda.co.jp/medical/products/holter_ecg/pdf/holter_ecg.pdf>].

"Digital Holter Recorder FM-190," Fukuda Denshi Co., Ltd., Retrieved Feb. 19, 2018, URL: <http://www.fukuda.co.jp/medical/products/holter_ecg/fm_190.html>.

Sep. 24, 2020 International Search Report issued in International Patent Application No. PCT/JP2020/024659.

Dec. 28, 2021 International Preliminary Report on Patentability issued in International Patent Application No. PCT/JP2020/024659.

\* cited by examiner

STORAGE CASE WITH BIOMEDICAL ELECTRODE PAD, AND BIOLOGICAL SIGNAL PROCESSING DEVICE INCLUDING STORAGE CASE WITH BIOMEDICAL ELECTRODE PAD

TECHNICAL FIELD

The present invention relates to a storage case with a biomedical electrode pad for storing a biological signal processing circuit unit that performs processing including recording and outputting biological electrical signals such as electrocardiographic signals and myoelectric signals detected from the skin by the biomedical electrode pad. The present invention also relates to a biological signal processing device including the storage case with the biomedical electrode pad.

BACKGROUND ART

Examples of conventionally known biomedical electrode pads that are attached to the skin of a living body to detect biological electrical signals from the skin include an event-specific waterproof electrode pad (TEC-07DEW) manufactured by Fukuda Denshi Co., Ltd., which is described in Non-Patent Document 1. This biomedical electrode pad is connected to a portable Holter electrocardiograph and used to monitor events by Holter electrocardiography. Specifically, it has an attachment sheet of a laterally elongated elliptical shape slightly wider at a central part, and on a lower surface of this attachment sheet, which is an adhesive surface, two detecting electrodes are disposed at both ends in a longitudinal direction, with one indifferent electrode at the center interposed therebetween. An electrode connecting pattern made of conductive metal is extended in a straight line from each electrode to near a side end of the central part of the attachment sheet, and three leads extending from a base end of a composite lead having connectors at leading ends are respectively connected to the electrode connecting patterns.

Besides, examples of conventionally known biological signal processing devices that perform processing including recording and outputting biological signals detected by a biomedical electrode pad like the one described above include a portable Holter electrocardiograph (FM-190) manufactured by Fukuda Denshi Co., Ltd., which is described in Non-Patent Document 2. This Holter electrocardiograph is stored in a portable case, and has the connectors of the composite lead of the above-described biomedical electrode pad connected thereto. Then, the Holter electrocardiograph is electrically connected to the three electrodes (the above-mentioned indifferent electrode and detecting electrodes) through the composite lead and the electrode connecting patterns. The portable case is worn around the arm of a living body, such as a patient to be examined by Holter electrocardiography, by a belt.

BACKGROUND ART DOCUMENTS

Patent Documents

Non-Patent Document 1: "Holter Electrocardiography Equipment Connection Guide" and "Lead, Relay, and Electrode Cords for Holter Electrocardiography" on pages 61 and 65, respectively, of "Holter Electrocardiography-Related Products," Fukuda Denshi Co., Ltd., downloaded on Feb. 15, 2018 from http://www.fukuda.cojp/medical/products/holter_ecg/pdf/holter_ecg.pdf Non Patent Document 2: "Digital Holter Recorder FM-190," Fukuda Denshi Co., Ltd., downloaded on Feb. 19, 2018 from http://www.fukuda.cojp/medical/products/holter_ecg/fm_190.html

SUMMARY OF THE INVENTION

Problem the Invention Attempts to Solve

However, the conventional storage case with the biomedical electrode pad and the biological signal processing device including the storage case with the biomedical electrode pad as described above still have some room for improvement in terms of wearability and the like. It is an object of the present invention to provide a storage case with a biomedical electrode pad and a biological signal processing device including the storage case with the biomedical electrode pad having a novel structure in which at least one improvement has been made with respect to common problems of improving wearability and wearing feeling.

Specifically, for example, it is difficult to obtain sufficient biological information by the above-described conventional sheet-shaped biomedical electrode pad because of the narrow range of detecting biological signals. Therefore, the present inventors have considered broadening the range of detecting biological signals by expanding the attachment sheet. It turned out, however, that doing so would create new problems: As stretching and contracting of the attachment sheet are restricted by the electrode connecting patterns that are extended in a straight line from both ends of the attachment sheet to near the side ends of the central part, the biomedical electrode pad fails to follow changes in shape of the limb due to body movement and comes easily off the skin. Moreover, the electrode connecting patterns break easily by undergoing excessive local deformation while stretching and contracting so as to follow changes in shape of the limb due to body movement.

Moreover, since the above-described conventional portable Holter electrocardiograph that is stored in the portable case worn around the arm of a living body, such as a patient to be examined, by the belt is connected to the biomedical electrode pad through the composite lead, another problem is that the biomedical electrode pad comes easily off the skin as a tensile force is applied to the leads due to body movement, such as movement of the arm and twisting of the body.

Therefore, in Japanese Patent Application No. 2018-061754, the present inventors proposed a biomedical electrode pad including: an attachment sheet that is elastically stretchable, has an electrically insulating property, and has, on a back surface side, an adhesive surface suitable to be attached to a skin of a living body; a plurality of electrodes that are located apart from one another on the back surface side of the attachment sheet and exposed to the back surface side; a plurality of connecting parts that are located at a central part on the back surface side of the attachment sheet and covered with electrical insulation while being exposed to a front surface side through openings of the attachment sheet; and electrode connecting wirings that are located on the back surface side of the attachment sheet and covered with electrical insulation, and that extend so as to bend in a bellows shape and electrically connect respective ones of the plurality of electrodes with corresponding ones of the plurality of connecting parts.

Furthermore, the present inventors proposed a biological signal processing device in combination with the above-mentioned biomedical electrode pad, the biological signal processing device including: a case that is fixed to a central part on a front surface side of an attachment sheet of a biomedical electrode pad, the attachment sheet having, on a back surface side, an adhesive surface suitable to be attached to skin of a living body and a plurality of electrodes; a biological signal processing circuit board that is stored inside the case and electrically connected to each of the plurality of electrodes on the back surface side of the biomedical electrode pad through a connecting member extending through the case and a central part of the attachment sheet, and that processes biological signals detected by the plurality of electrodes and outputs a processing result; and a battery that is stored inside the case and supplies electricity to the biological signal processing circuit board.

When the present inventors further researched the combination of this biological signal processing device and the biomedical electrode pad, it turned out that it is preferable to be able to attach and detach the case and the biomedical electrode pad to and from the biological signal processing circuit board, and to sterilize and clean the case and the biomedical electrode pad, and to replace them when damaged.

Further, in the combination of the biological signal processing device and the biomedical electrode pad, a case for storing the biological signal processing circuit board is attached and fixed to the surface of the biomedical electrode pad without any gap, but it turned out that it is preferable to leave a gap for ventilation between the case and the surface of the biomedical electrode pad because, when a water vapor permeable sheet is used for the biomedical electrode pad worn for a long time, it is possible to prevent the skin from getting sweaty.

Moreover, it turned out that, in order to realize good wearability and wearing feeling, it is desirable that the back surface of the biomedical electrode pad, which is to be in contact with the skin, is as soft as possible for the attachment portion of the storage case.

Means for Solving the Problem

Hereinafter, preferred embodiments for grasping the present invention will be described. However, each preferred embodiment described below is exemplary and can be appropriately combined with each other. Besides, a plurality of elements described in each preferred embodiment can be recognized and adopted as independently as possible, or can also be appropriately combined with any element described in other preferred embodiments. By so doing, in the present invention, various other preferred embodiments can be realized without being limited to those described below.

A first preferred embodiment provides a storage case with a biomedical electrode pad attached, the biomedical electrode pad comprising an attachment sheet being provided with a plurality of electrodes on a back surface and having flexibility, the back surface being configured to be attached to a skin of a living body, the storage case with the biomedical electrode pad being configured to store a biological signal processing circuit unit for processing a biological electrical signal detected by the biomedical electrode pad, wherein a case body having a storage area for the biological signal processing circuit unit is arranged on a front surface side of the attachment sheet and attached to the attachment sheet, the storage area is provided to the case body in an openable and closable manner, and the biological signal processing circuit unit is detachable with respect to the storage area.

A second preferred embodiment provides the storage case with the biomedical electrode pad according to the first preferred embodiment, wherein the case body has a watertight structure with the storage area closed.

A third preferred embodiment provides the storage case with the biomedical electrode pad according to the first or second preferred embodiment, wherein the case body includes a connecting member configured to electrically connect the electrodes and the biological signal processing circuit unit, the connecting member penetrating through a case wall of the case body.

A fourth preferred embodiment provides a storage case with a biomedical electrode pad attached, the biomedical electrode pad comprising an attachment sheet being provided with a plurality of electrodes on a back surface and having flexibility, the back surface being configured to be attached to a skin of a living body, the storage case with the biomedical electrode pad being configured to store a biological signal processing circuit unit for processing a biological electrical signal detected by the biomedical electrode pad, wherein the attachment sheet has water vapor permeability, a case body for storing the biological signal processing circuit unit is arranged on a front surface side of the attachment sheet, and a ventilation gap that is open to an external space is provided between the case body and the attachment sheet.

A fifth preferred embodiment provides the storage case with the biomedical electrode pad according to the fourth preferred embodiment, wherein a plurality of leg parts fixing the case body and the attachment sheet to each other are provided, and the ventilation gap is formed between the plurality of leg parts.

A sixth preferred embodiment provides the storage case with the biomedical electrode pad according to any one of the first to fifth preferred embodiments, wherein the attachment sheet has elasticity that is stretchable in a planar direction, and at least a part of a current path that is conductive with respect to the electrodes is formed by a stretchable portion on a surface of the attachment sheet.

A seventh preferred embodiment provides the storage case with the biomedical electrode pad according to any one of the first to sixth preferred embodiments, wherein the case body having the storage area for the biological signal processing circuit unit is attached to the attachment sheet in a detachable manner.

An eighth preferred embodiment provides a storage case with a biomedical electrode pad attached, the biomedical electrode pad being configured to be attached to a skin of a living body and used to detect a biological electrical signal from the skin, the storage case with the biomedical electrode pad being configured to watertightly and detachably store a biological signal processing circuit unit inside, the biological signal processing circuit unit having a battery as a power source and processing the biological electrical signal detected by the biomedical electrode pad, wherein the biomedical electrode pad comprises:
an attachment sheet having water vapor permeability, the attachment sheet being elastically stretchable and having an electrically insulating property while including, on a back surface side, an adhesive surface suitable to be attached to the skin of the living body;
a plurality of electrodes located apart from one another on the back surface side of the attachment sheet and exposed to the back surface side;

a plurality of connecting parts that are located at a central part of the back surface side of the attachment sheet and covered with electrical insulation while being exposed to a front surface side through an opening of the attachment sheet; and an electrode connecting wiring that is located on the back surface side of the attachment sheet and covered with electrical insulation while having a stretchable portion in at least a part of the electrode connecting wiring, and that electrically connects the plurality of electrodes with corresponding ones of the plurality of connecting parts, and the storage case comprises:

a receptacle case including a plurality of leg parts fixed to a central part of the front surface side of the attachment sheet of the biomedical electrode pad, and forming, between the leg parts, a gap partially between a front surface of the attachment sheet and the receptacle case;

a cover case that is watertightly and detachably fitted to the receptacle case; and an elastic connecting member penetrating through an opening in each of the leg parts of the receptacle case and through the opening at the central part of the attachment sheet to be located within the openings such that the elastic connecting member is elastically in contact with each of the plurality of connecting parts exposed from the opening at the central part of the attachment sheet to the front surface side of the attachment sheet and with the biological signal processing circuit unit in the storage case to electrically connect the each of the plurality of connecting parts and the biological signal processing circuit unit.

A ninth preferred embodiment provides the storage case with the biomedical electrode pad according to the eighth preferred embodiment, wherein the plurality of electrodes include an indifferent electrode and a plurality of detecting electrodes.

A tenth preferred embodiment provides the storage case with the biomedical electrode pad according to the eighth or ninth preferred embodiment, wherein a flexible wiring board is constituted by: a resin substrate; the plurality of electrodes arranged on a lower surface of the resin substrate; the plurality of connecting parts arranged on an upper surface of the resin substrate; and the electrode connecting wiring arranged on the upper surface of the resin substrate, an end part of the electrode connecting wiring penetrating through the resin substrate to electrically connect the plurality of electrodes with corresponding ones of the plurality of connecting parts.

An eleventh preferred embodiment provides the storage case with the biomedical electrode pad according to any one of the eighth to tenth preferred embodiments, wherein the plurality of leg parts of the receptacle case each include a proximal part fixed to the receptacle case and a distal end part detachably fitted to the proximal part while being fixed to the central part of the front surface side of the attachment sheet of the biomedical electrode pad.

A twelfth preferred embodiment provides the storage case with the biomedical electrode pad according to any one of the eighth to eleventh preferred embodiments, wherein at least one of the receptacle case and the cover case is made of a soft resin.

A thirteenth preferred embodiment provides a biological signal processing device including the storage case with the biomedical electrode pad according to any one of the first to twelfth preferred embodiments, wherein the biological signal processing circuit unit is stored inside the storage case with the biomedical electrode pad.

Effect of the Invention

According to the storage case with the biomedical electrode pad related to the first preferred embodiment, the case body, which tends to be less flexible than the attachment sheet, is arranged on the front surface side of the flexible attachment sheet. With this arrangement, the case body is prevented from coming into direct contact with the skin, and a sense of discomfort at the time of attachment is suppressed, thereby improving the wearability and the wearing feeling.

In addition, the biological signal processing circuit unit equipped with an electric circuit is detachable. Thus, with the biological signal processing circuit unit, which is not water-resistant in general, is detached, it is easy to perform cleaning, sterilizing and the like on the attachment sheet and storage case (including the case body). This makes it possible to improve the wearability and the wearing feeling by maintaining the cleanliness and the like in the attached state. Moreover, by detaching the biological signal processing circuit unit, it is also possible to replace the attachment sheet and the storage case, and to reuse the biological signal processing circuit unit.

In the storage case with the biomedical electrode pad according to the second preferred embodiment, the case body has a watertight structure. Thus, even if there is a part such as an energizing member that dislikes moisture etc. in the storage area, processing such as cleaning, sterilization and the like can be easily performed with the case body closed. In addition, even if the biological signal processing circuit unit is still mounted in the case body, by the watertightness of the storage area being ensured, it is possible to prevent occurrence of problems when water or the like is accidentally splashed during attachment on the living body, as well as to allow showering and bathing while the biological signal processing circuit unit is attached to the living body. Also, by a high degree of watertightness being achieved, it is also possible to perform disinfection, sterilization and the like while the biological signal processing circuit is attached. Furthermore, by mounting the biological signal processing circuit unit in the storage area having the watertight structure, the protection of the biological signal processing circuit unit is excellent as well, and the storage area is more suitable for reusing the biological signal processing circuit unit.

In the storage case with the biomedical electrode pad according to the third preferred embodiment, the connecting member for energizing the electrode on the back surface side of the attachment sheet to the biological signal processing circuit unit in the case body can be provided with a simple structure or a short path. In particular, by providing the connecting member so as to penetrate through the bottom wall portion of the case body overlapped with the attachment sheet, it is possible to avoid direct exposure of the connecting member to the outside. Further, for example, by insert-molding the connecting member into the case body or providing a sealing material at the arrangement position of the connecting member, it is possible to easily realize providing the connecting member while achieving the watertightness of the case body.

In the storage case with the biomedical electrode pad according to the fourth preferred embodiment, the attachment sheet having water vapor permeability can reduce or avoid sweatiness and the like of the skin of the living body, which is the attachment surface. Further, since the case body, which tends to be less flexible than the attachment sheet, is arranged on the front surface side of the flexible attachment sheet, it is possible to suppress a sense of discomfort during attachment due to direct contact of the case body with the skin. In addition, even in the attachment area of the case body on the attachment sheet, the water vapor permeability of the attachment sheet can be maintained through the ventilation gap, thereby further improving the wearability and the wearing feeling.

In the storage case with the biomedical electrode pad according to the fifth preferred embodiment, it is possible to efficiently form the ventilation gap while ensuring the strength and stability of fixing the case body to the attachment sheet by the plurality of leg parts.

In the storage case with the biomedical electrode pad according to the sixth preferred embodiment, by providing a stretchable portion in the current path, the original flexibility and elasticity of the attachment sheet can be prevented from being hindered by the current path, thereby improving the wearability and the wearing feeling. The stretchable portion can be realized by, for example, a meandering shape, an accordion-like shape, a bent shape, or the like in the length direction of the current path in which stretching and contracting are allowed due to curving deformation, as will be described later. Alternatively, elasticity may be imparted to the current path itself by blending a conductive material comprising powder, filler or the like made of carbon, metal, or the like into rubber or elastomer, or by using an ionic conductive polymer or the like.

In the storage case with the biomedical electrode pad according to the seventh preferred embodiment, by detaching the case body, the case body can be separated from the attachment sheet together with the biological signal processing circuit unit stored in the case body, for example. Therefore, it is possible to repair or replace only the case body, as well as to reuse the case body together with the biological signal processing circuit unit.

The storage case with the biomedical electrode pad according to the eighth preferred embodiment is attached so that the adhesive surface on the back surface side of the attachment sheet is overlapped with the detection position of the biological signal on the skin of the subject. Under such an attached state, the plurality of electrodes located apart from one another on the back surface side of the attachment sheet and exposed to the back surface side detect a biological electrical signal from the skin of the subject. The detected biological signal is transmitted to the plurality of connecting parts that are located at the central part of the back surface side of the attachment sheet and covered with electrical insulation through the electrode connecting wiring that is located on the back surface side of the attachment sheet and covered with electrical insulation. On the other hand, there is provided the elastic connecting member penetrating through the opening of the receptacle case and through the opening at the central part of the attachment sheet, and the elastic connecting member electrically connects the plurality of connecting parts, which are exposed to the a front surface side of the attachment sheet, with the biological signal processing circuit unit stored in the storage case. The biological signal processing circuit unit operates by being supplied with power from a battery, and makes it possible to process the biological signal detected from the skin of the subject by the plurality of electrodes, as well as to output the processing result by recoding on a recording medium, by transmitting wirelessly, and the like.

In addition, since the attachment sheet is elastically stretchable and has an electrically insulating property, the attachment sheet can stretch and contract by following the deformation of the limb due to body movement so as to maintain a state of close contact with the skin. Further, the electrode connecting wiring that electrically connects the plurality of electrodes with corresponding ones of the plurality of connecting parts has the stretchable portion in at least a part thereof. Thus, even if the electrode connecting wiring, which follows the deformation of the limb due to body movement, stretches and contracts, disconnection due to excessive partial deformation is less likely to occur. Moreover, the attachment sheet has water vapor permeability, while the receptacle case has the plurality of leg parts fixed to the central part of the front surface side of the attachment sheet of the biomedical electrode pad and forms, between the leg parts, the gap partially between the front surface of the attachment sheet and the receptacle case to ensure breathability. Thus, it is possible to prevent the skin from getting sweaty even when the attachment sheet is attached to the skin for a long time.

Therefore, according to the storage case with the biomedical electrode pad according to the eighth preferred embodiment, the storage case with the biomedical electrode pad is attached to and detached from the biological signal processing circuit by the cover case being attached to and detached from the receptacle case, so that the storage case and the biomedical electrode pad can be easily sterilized and cleaned, or replaced when damaged. Moreover, even if the attachment sheet is expanded more than before to expand the range in which the biological signal can be detected, the detection of the biological signal from the skin by the plurality of electrodes can be sustained for a long period of time, regardless of the deformation of the limb due to body movement, thereby also improving the wearing feeling of the attachment sheet on the skin at that time.

Besides, with the biological signal processing device according to the thirteenth preferred embodiment, which uses the storage case with the biomedical electrode pad according to the eighth preferred embodiment, the biological signal processing circuit unit is stored inside of the storage case in a watertight and detachable manner. Thus, while the above-described working effects of the storage case with the biomedical electrode pad are achieved, the biological signal processing circuit unit in the storage case is able to process the biological signal detected from the skin of the subject by the electrodes of the biomedical electrode pad, as well as to output the processing result by recording on a recording medium, by transmitting wirelessly, and the like.

Also, the storage case with the biomedical electrode pad of the invention according to the eighth preferred embodiment or the like may suitably adopt a preferred embodiment in which the plurality of leg parts of the receptacle case each include a proximal part fixed to the receptacle case and a distal end part detachably fitted to the proximal part while being fixed to the central part of the front surface side of the attachment sheet of the biomedical electrode pad. Such a preferred embodiment is favorable since the receptacle case and the biomedical electrode pad can be easily separated between the proximal part and the distal end part of the leg part, so that only one of them can be sterilized and cleaned, or replaced when damaged as necessary.

Additionally, the storage case with the biomedical electrode pad of the invention according to the eighth preferred embodiment or the like may suitably adopt a preferred embodiment in which at least one of the receptacle case and the cover case is made of a soft resin. Such a preferred embodiment is favorable since it is possible to easily fit the cover case to the receptacle case in a watertight and detachable manner.

EMBODIMENTS FOR CARRYING OUT THE INVENTION

Figure 1:
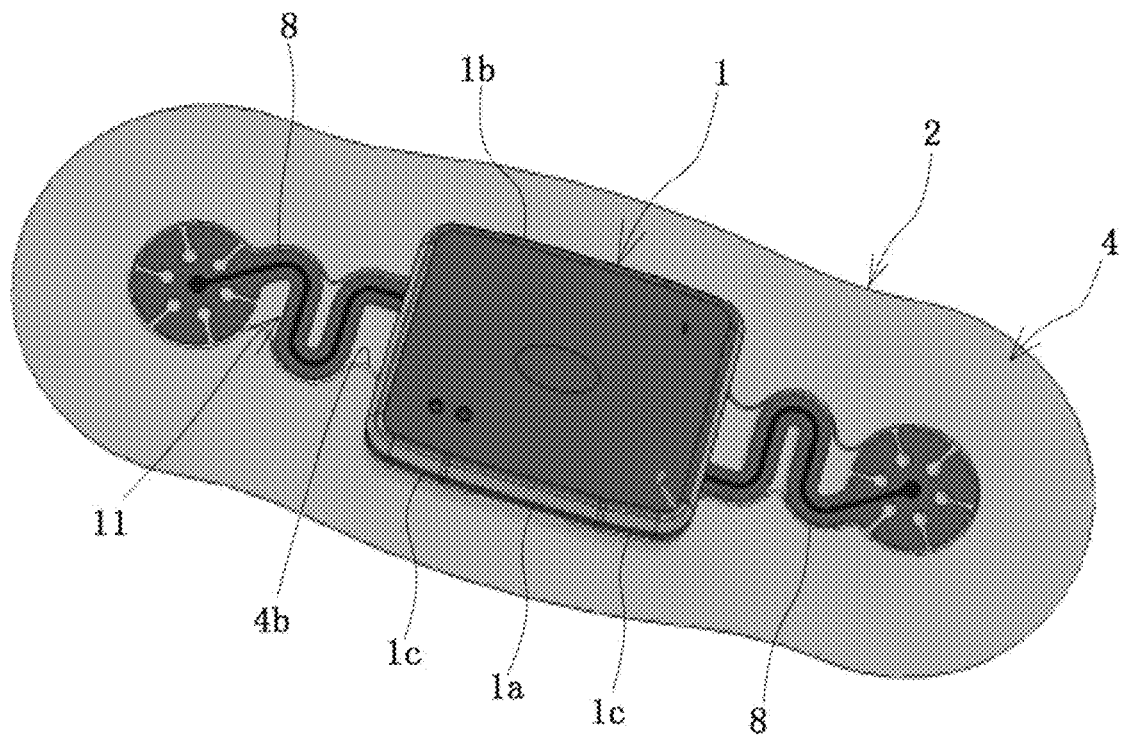
FIG. 1 is a perspective view showing a storage case with a biomedical electrode pad according to a first practical embodiment of the present invention and a biological signal processing device including the storage case according to a first practical embodiment of the present invention in the form of a Holter electrocardiograph, which are viewed from a front surface side of the biomedical electrode pad.
Figure 2:
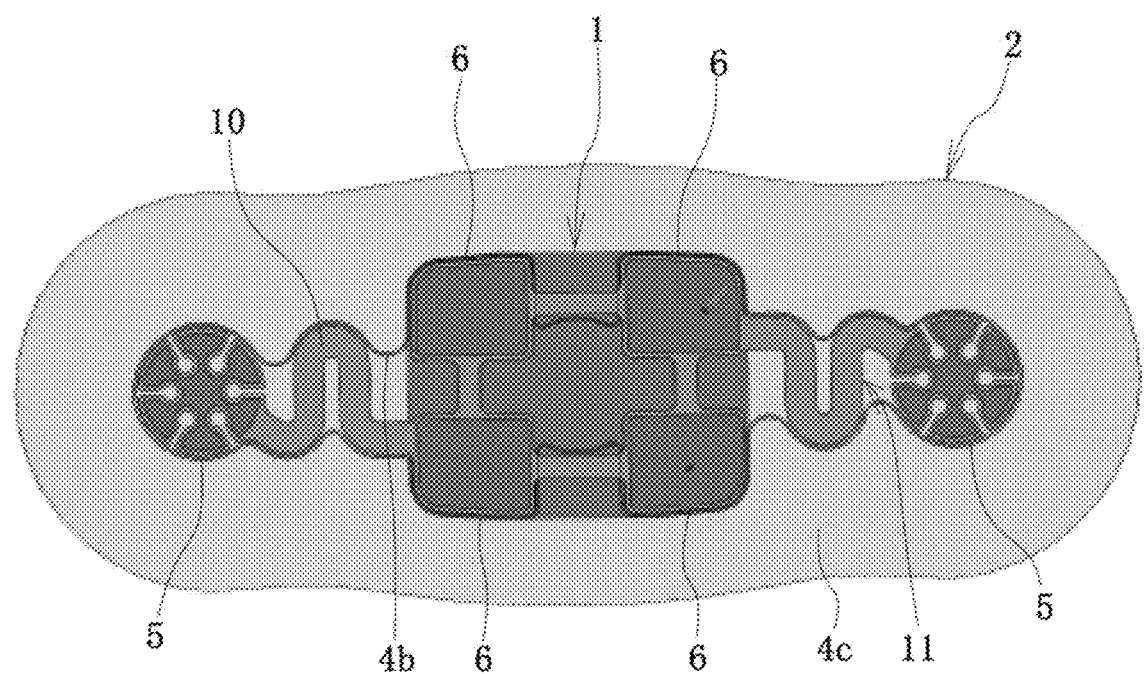
FIG. 2 is a bottom view showing the storage case with the biomedical electrode pad of the said practical embodiment and the Holter electrocardiograph including the storage case of the said practical embodiment, which are viewed from a back surface side of the biomedical electrode pad.
Figure 3:
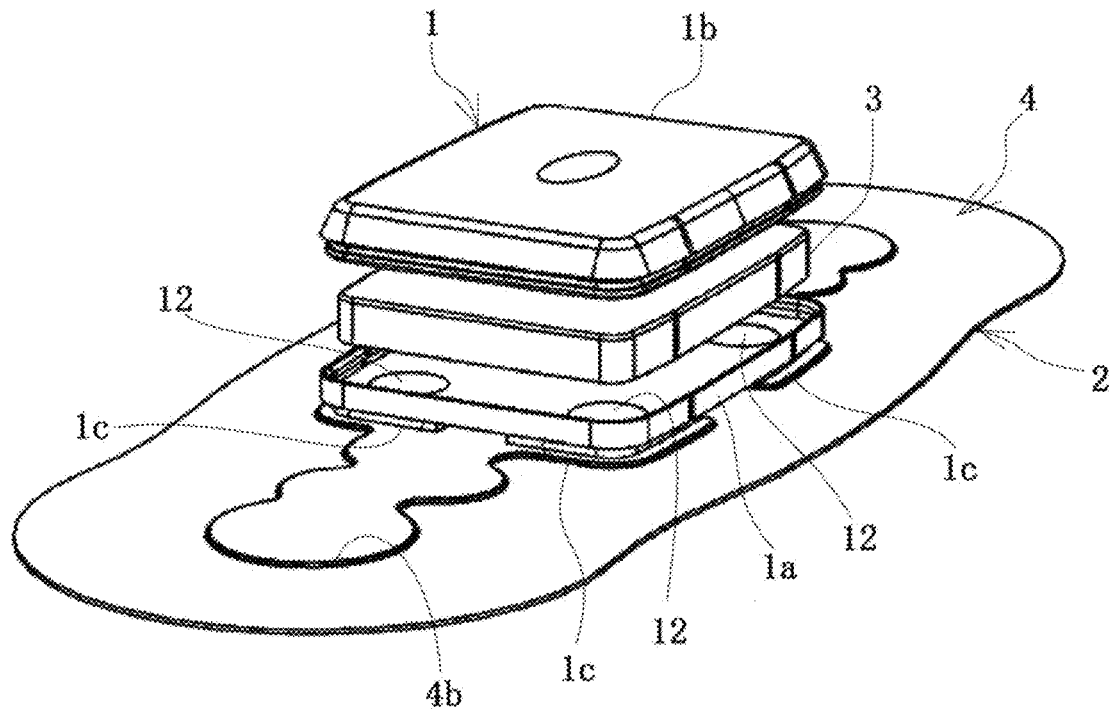
FIG. 3 is an exploded perspective view showing the storage case with the biomedical electrode pad of the said practical embodiment and the Holter electrocardiograph including the storage case of the said practical embodiment, which are viewed from the front surface side of the biomedical electrode pad.
Figure 4:
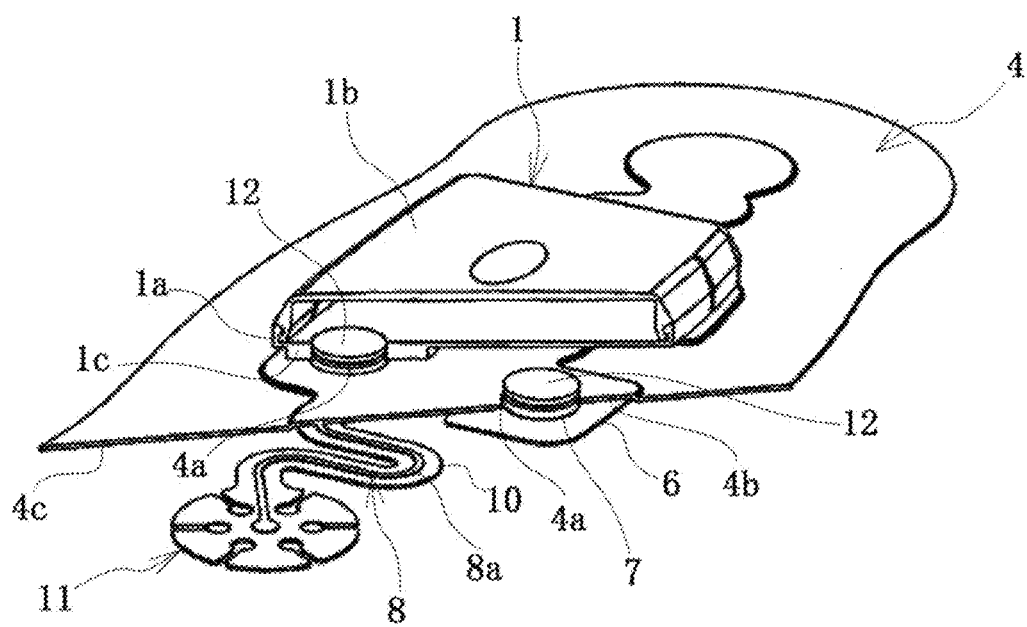
FIG. 4 is a perspective view showing the storage case with the biomedical electrode pad of the said practical embodiment by cutting out a part thereof, which is viewed from the front surface side of the biomedical electrode pad.

Hereinafter, practical embodiments of the present invention will be described in detail with reference to the drawings by way of examples. Here, FIG. 1 is a perspective view showing a storage case with a biomedical electrode pad according to a first practical embodiment of the present invention and a biological signal processing device including the storage case according to a first practical embodiment of the present invention in the form of a Holter electrocardiograph, which are viewed from a front surface side of the biomedical electrode pad. FIG. 2 is a bottom view showing the storage case with the biomedical electrode pad of the said practical embodiment and the Holter electrocardiograph including the storage case of the said practical embodiment, which are viewed from a back surface side of the biomedical electrode pad. FIG. 3 is an exploded perspective view showing the storage case with the biomedical electrode pad of the said practical embodiment and the Holter electrocardiograph including the storage case of the said practical embodiment, which are viewed from the front surface side of the biomedical electrode pad. FIG. 4 is a perspective view showing the storage case with the biomedical electrode pad of the said practical embodiment by cutting out a part thereof, which is viewed from the front surface side of the biomedical electrode pad.

Figure 5:
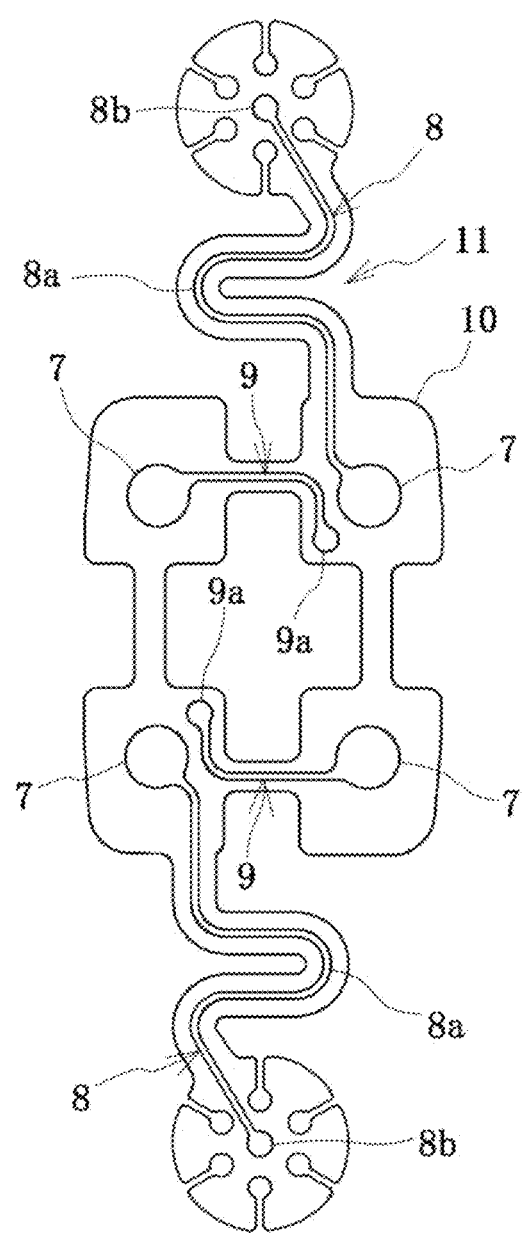
FIG. 5 is a plan view showing a structure of a flexible wiring board of the biomedical electrode pad of the storage case with the biomedical electrode pad of the said practical embodiment and the Holter electrocardiograph including the storage case of the said practical embodiment.
Figure 6:
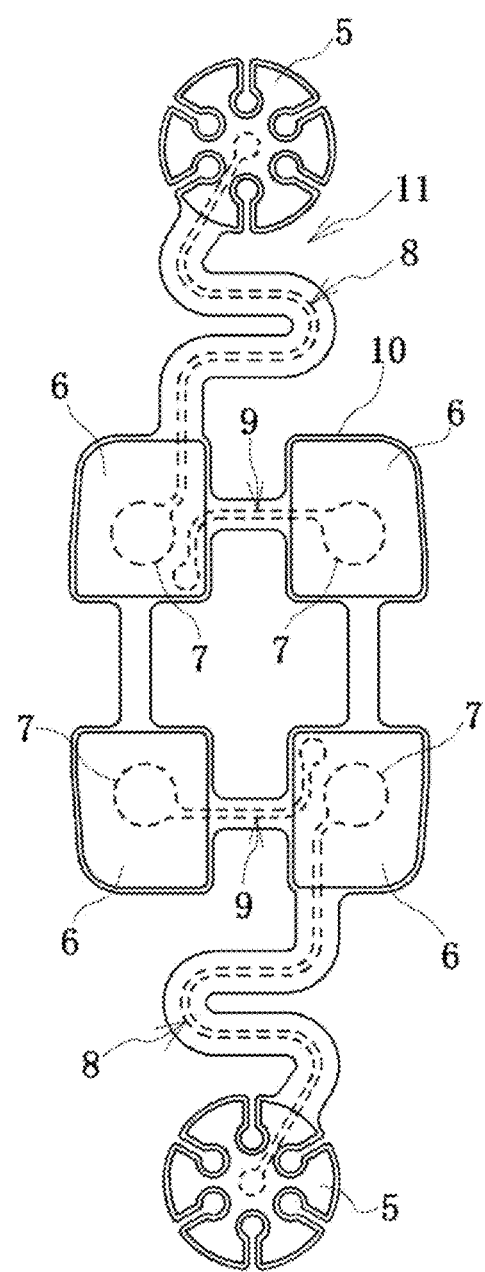
FIG. 6 is a bottom view showing the structure of the flexible wiring board of the storage case with the biomedical electrode pad of the said practical embodiment and the Holter electrocardiograph including the storage case of the said practical embodiment.
Figure 7:
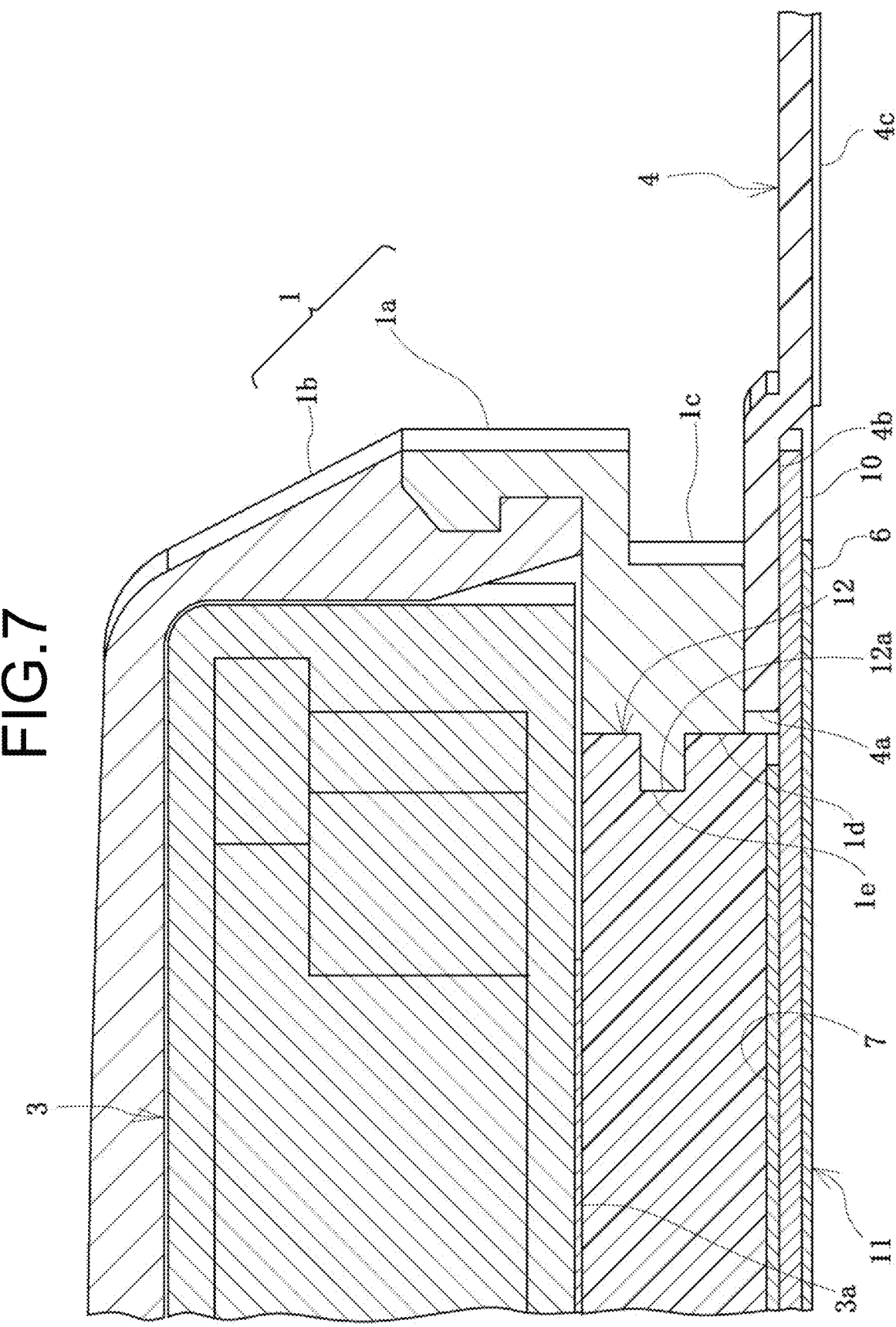
FIG. 7 is an enlarged cross-sectional view showing parts of the storage case with the biomedical electrode pad of the said practical embodiment and the Holter electrocardiograph including the storage case of the said practical embodiment.

Further, FIG. 5 is a plan view showing a structure of a flexible wiring board of the biomedical electrode pad of the storage case with the biomedical electrode pad of the said practical embodiment and the Holter electrocardiograph including the storage case of the said practical embodiment. FIG. 6 is a bottom view showing the structure of the flexible wiring board of the storage case with the biomedical electrode pad of the said practical embodiment and the Holter electrocardiograph including the storage case of the said practical embodiment. FIG. 7 is an enlarged cross-sectional view showing parts of the storage case with the biomedical electrode pad of the said practical embodiment and the Holter electrocardiograph including the storage case of the said practical embodiment.

A storage case 1 with a biomedical electrode pad according to the said practical embodiment is a storage case including a biomedical electrode pad 2 that is attached to a skin of a living body and is used to detect an electrocardiographic signal as an biological electrical signal from the skin.

The storage case 1 with the biomedical electrode pad is for storing an electrocardiographic signal processing circuit unit 3 serving as a biological signal processing circuit unit in a watertight and detachable manner. The electrocardiographic signal processing circuit unit 3 includes an electrocardiographic signal processing circuit having a normal CPU, memory, etc., which is operated by power supply from a battery such as a button battery having as a power source. The electrocardiographic signal processing circuit can input and record the electrocardiographic signal detected by the biomedical electrode pad 2 over a fixed time such as 24 hours. Besides, the electrocardiographic signal processing circuit is able to output the recorded electrocardiographic signal by wire or wirelessly in response to an external command signal, or by extracting a card-type recording medium on which the electrocardiographic signal is recorded.

The biomedical electrode pad 2 in the storage case 1 with the biomedical electrode pad of this practical embodiment is elastically stretchable and has an electrically insulating property, and includes on its back surface side a water vapor permeable attachment sheet 4 having an adhesive surface 4c suitable for being attached to the skin of the living body.

On the back surface side of the attachment sheet 4, arranged are a plurality of electrodes located apart from one another and exposed to the back surface side. That is, in the illustrated example, as a plurality of electrodes exposed to the back surface side, two detecting electrodes 5 at both ends in the longitudinal direction of the attachment sheet 4 and four indifferent electrodes 6 at the central part are provided.

Further, the attachment sheet 4 includes a plurality of (four in the illustrated example) connecting parts 7 that are located in the central part on the back surface side thereof and are covered with electrical insulation while being exposed to the front surface side through openings of the attachment sheet 4. Further, the attachment sheet 4 includes two detecting electrode connecting wirings 8 which are located on the back surface side thereof and are covered with electrical insulation while having a meandering shape stretchable portion 8a in a part thereof. These two detecting electrode connecting wirings 8 that electrically connect two detecting electrodes 5 located at both ends of the attachment sheet 4 with the corresponding two connecting parts 7 on a diagonal line among the four connecting parts 7. Moreover, the attachment sheet 4 includes two indifferent electrode connecting wirings 9 each electrically connecting the two indifferent electrodes 6 arranged in the width direction of the attachment sheet 4 with each other among the four indifferent electrodes 6. Each pair of the indifferent electrodes 6 connected by the corresponding indifferent electrode connecting wiring 9 is electrically connected to the corresponding one of two connecting parts 7 to which the detecting electrode connecting wiring 8 is not connected among the four connecting parts 7.

Specifically, the biomedical electrode pad 2 has a resin substrate 10 that is elastically stretchable and has an electrically insulating property. On the lower surface of the resin substrate 10, the two detecting electrodes 5 at both ends (referring to both ends in the longitudinal direction, which is the left-right direction in FIG. 2) and the four indifferent electrodes 6 at the central part are formed by, for example, a silver-silver chloride (Ag/Agcl) layer that is less likely to be oxidized by contact with the skin. Further, on the upper surface of the resin substrate 10, the detecting electrode connecting wirings 8 and the indifferent electrode connecting wirings 9 are also formed by a silver-silver chloride layer or a copper layer. The detecting electrodes 5, the indifferent electrodes 6, the detecting electrode connecting wirings 8, the indifferent electrode connecting wirings 9, and the resin substrate 10 constitute a flexible wiring board 11.

The resin substrate 10 can be formed of, for example, a polyimide sheet, a polyethylene terephthalate (PET) film, or the like. Further, the silver-silver chloride layer can be formed at a predetermined position in a predetermined shape by, for example, applying a known silver-silver chloride paste with a printer or the like and drying and curing the paste. The copper layer can be formed at a predetermined position in a predetermined shape by using, for example, a plating method, an etching method, or the like used for manufacturing a printed wiring board.

Penetration parts 8b are respectively formed at the distal ends of the two detecting electrode connecting wirings 8. These penetration parts 8b are electrically connected to the two detecting electrodes 5 under the penetration parts 8b through penetration holes formed in the resin substrate 10.

Besides, penetration parts 9a are respectively formed at the distal ends of the two indifferent electrode connecting wirings 9. These penetration parts 9a are electrically connected to the indifferent electrodes 6 under the penetration parts 9a through the penetration holes formed in the resin substrate 10.

Moreover, the remaining two connecting parts 7 (the two connecting parts 7 to which the detecting electrode connecting wirings 8 are not connected), to which the two indifferent electrode connecting wirings 9 are connected, are electrically connected to the indifferent electrodes 6 under the connecting parts 7 through the penetration holes formed in the resin substrate 10. With this configuration, the two indifferent electrodes 6 arranged in the width direction (the short-side direction, which is the vertical direction in FIG. 2) of the attachment sheet 4 are also electrically connected to each other by the two indifferent electrode connecting wirings 9.

The storage case 1 includes a receptacle case 1a located on the lower side close to the attachment sheet 4, and a cover case 1b located on the upper side far from the attachment sheet 4.

The receptacle case 1a includes a plurality of (four in the illustrated example) leg parts 1c that are watertightly fixed to the central part of the front surface side of the attachment sheet 4 of the biomedical electrode pad 2. Further, between the leg parts 1c, a gap is formed partially between opposed faces (between the overlapped surfaces) of the front surface of the attachment sheet 4 and the receptacle case 1a.

As shown in FIG. 4, by the cover case 1b being overlapped from the outer direction of the receptacle case 1a (the direction away from the attachment sheet 4), the cover case 1b is fitted and attached so that the outer peripheral walls of both the receptacle case 1a and the cover case 1b are watertight and detachable.

Four openings 4a are formed in the central part of the attachment sheet 4. Through these four openings 4a, the four connecting parts 7 are respectively exposed to the front surface side of the attachment sheet 4. Besides, the four leg parts 1c of the receptacle case 1a are provided at positions corresponding to the four openings 4a of the attachment sheet 4, and the leg parts 1c are arranged so as to cover the openings 4a from the front surface side of the attachment sheet 4. Furthermore, an opening 1d is formed in each leg part 1c so as to penetrate the central portion thereof, and an elastic connecting member 12 made of an elastic material having conductivity is attached to the opening 1d in a fitted state.

The lower surfaces of the four elastic connecting members 12 provided to the four leg parts 1c are exposed in the four openings 4a of the attachment sheet 4. Further, each upper surface of the four elastic connecting members 12 is exposed to the bottom surface of the receptacle case 1a through the four openings 1d provided in the receptacle case 1a.

Then, the connecting parts 7 are respectively overlapped and in contact with the lower surfaces of the elastic connecting members 12 from the back surface side of the attachment sheet 4 through the openings 4a of the attachment sheet 4. On the other hand, on the upper surface of each elastic connecting member 12, each one of the four electrodes 3a, which is formed on the lower surface of the electrocardiographic signal processing circuit unit 3 stored and mounted in the storage area of the storage case 1, is overlapped and in contact.

That is, the four elastic connecting members 12 are located within the respective openings 1d of the leg parts 1c of the receptacle case 1a and the respective openings 4a of the central part of the attachment sheet 4 so as to penetrate therethrough. Then, these four elastic connecting members 12 are elastically in contact with the connecting parts 7 and the four electrodes 3a on the lower surface of the electrocardiographic signal processing circuit unit 3 in the storage case 1, and maintain these four pairs of the connecting part 7 and the electrode 3a in an electrically connected state.

Regarding the receptacle case 1a and the cover case 1b, at least one of them, that is, both of them here are made of a soft resin such as polyethylene and polypropylene. Due to elastic deformation of the soft resin, the receptacle case 1a and the cover case 1b can be fitted watertightly and detachably with respect to each other as shown in the cross section in FIG. 7. The elastic connecting member 12 is made of, for example, a rubber-like elastic body. As shown in the cross section in FIG. 7, in the illustrated example, the elastic connecting member 12 may have an outer peripheral annular groove 12a that closely fits with an inside flange 1e protruding into the opening 1d of the leg part 1c, and may be watertightly fitted in the opening 1d. Alternatively, the elastic connecting member 12 may be placed at a position in the opening 1d of the injection molding die of the receptacle case 1a and be insert-molded integrally with the receptacle case 1a. Furthermore, the elastic connecting member 12 may be, for example, a metal coil-shaped or plate-shaped spring member. The watertightness in the storage area inside the case body (the receptacle case 1a and the cover case 1b) at the arrangement portion of the elastic connecting member 12 can also be ensured by, for example, the openings 4a of the attachment sheet 4 being covered and sealed by the leg parts 1c of the receptacle case 1a and the resin substrate 10 from both sides.

A shallow recess 4b extending in the longitudinal direction of the attachment sheet 4 is formed on the back surface side of the attachment sheet 4 so as to store the flexible wiring board 11. Besides, an adhesive surface 4c is provided on the back surface of the attachment sheet 4 so as to surround the recess 4b.

Regarding the storage case 1 with the biomedical electrode pad of the above practical embodiment, the attachment sheet 4 of the biomedical electrode pad 2 is mounted on the adhesive surface 4c on the back surface side at the electrocardiographic signal detection position of the skin of a subject. Under such a mounted state, the plurality of electrodes (the two detecting electrodes 5 at both ends and the four indifferent electrodes 6 at the central part), which are located apart from one another on the back surface side of the attachment sheet 4 and are exposed to the back surface side thereof, detect an electrocardiographic signal from the skin of the subject. The detected electrocardiographic signal passes the electrode connecting wirings 8, 9, which are located on the back surface side of the attachment sheet 4 and covered with electrical insulation, and is transmitted to the four connecting parts 7, which are located at the central part of the back surface side of the attachment sheet 4 and covered with electrical insulation. Moreover, the elastic connecting members 12 penetrating the openings 1d of the leg parts 1c of the receptacle case 1a and the openings 4a at the central part of the attachment sheet 4 are elastically in contact with those connecting parts 7 exposed to the front surface side of the attachment sheet 4 and the electrocardiographic signal processing circuit unit 3 stored in the storage case 1, and electrically connect the connecting parts 7 and the electrocardiographic signal processing circuit unit 3. Therefore, the detected electrocardiographic signal is transmitted from the connecting parts 7 to the electrocardiographic signal processing circuit unit 3 through the elastic connecting members 12. As a result, by the power supply from the battery, the electrocardiographic signal processing circuit unit 3 is able to process the electrocardiographic signal detected from the skin of the subject by the detecting electrodes 5 and the indifferent electrodes 6, as well as to output the processing result by recoding on a recording medium such as a memory, by transmitting wirelessly, by extracting a card-type recording medium, and the like.

Also, the attachment sheet 4 is elastically stretchable and has an electrically insulating property. Thus, the attachment sheet 4 can stretch and contract by following the deformation of the limb due to body movement so as to maintain a state of close contact with the skin.

Further, the detecting electrode connecting wirings 8 that electrically connect the two detecting electrodes 5 and the respective two connecting parts 7 have a stretchable portion 8a in a part thereof. Thus, even if the detecting electrode connecting wiring 8, which follows the deformation of the limb due to body movement, stretches and contracts, disconnection due to excessive partial deformation is less likely to occur, while avoiding excessive restriction of deformation of the attachment sheet 4 due to the detecting electrode connecting wiring 8.

Besides, the attachment sheet 4 has water vapor permeability, while the receptacle case 1a has the four leg parts 1c fixed to the central part of the front surface side of the attachment sheet 4 and forms, between the leg parts 1c, a gap partially between the front surface of the attachment sheet 4 and the receptacle case 1a to ensure breathability. Thus, it is possible to prevent the skin from getting sweaty even when the attachment sheet 4 is attached to the skin for a long time.

Therefore, according to the storage case 1 with the biomedical electrode pad of this practical embodiment, the cover case 1b is attached to and detached from the receptacle case 1a so that the storage case 1 with the biomedical electrode pad is attached to and detached from the electrocardiographic signal processing circuit unit 3. By so doing, the storage case 1 and the biomedical electrode pad 2 can be easily sterilized and cleaned, or replaced when damaged. Moreover, even if the attachment sheet 4 is expanded more than before to expand the range in which the electrocardiographic signal can be detected, the detection of the electrocardiographic signal from the skin by the two detecting electrodes 5 and the four indifferent electrodes 6 can be sustained for a long period of time, regardless of the deformation of the limb due to body movement, thereby also improving the wearing feeling of the attachment sheet 4 on the skin at that time.

Furthermore, according to the storage case 1 with the biomedical electrode pad of this practical embodiment, at least one of the receptacle case 1a and the cover case 1b, preferably both of them, is formed of a soft resin. This makes it possible to easily fit the cover case 1b to the receptacle case 1a in a watertight and detachable manner. By forming the receptacle case 1a using a soft resin, it is possible to reduce deformation restraint of the receptacle case 1a with respect to the attachment sheet 4, thereby further improving the wearing feeling.

According to the Holter electrocardiograph of this practical embodiment using the storage case 1 with the biomedical electrode pad, the electrocardiographic signal processing circuit unit 3 is watertightly and detachably stored inside the storage case 1. Thus, while the above-described working effects of the storage case 1 with the biomedical electrode pad are achieved, the electrocardiographic signal processing circuit unit 3 in the storage case 1 is able to process the electrocardiographic signal detected from the skin of the subject by the two detecting electrodes 5 and the four indifferent electrodes 6 of the biomedical electrode pad 2, as well as to output the processing result by recording on a recording medium, by transmitting wirelessly, and the like, more stably by avoiding operation mistakes due to inadvertent water exposure etc.

In the present practical embodiment, the two connecting parts 7 at the upper left and the lower right in FIG. 5 are connected to the two electrodes 3a on one diagonal line on the lower surface of the electrocardiographic signal processing circuit unit 3 in the storage case 1. Meanwhile, the two connecting parts 7 at the upper right and the lower left in FIG. 5 are connected to the two electrodes 3a on the other diagonal line of the lower surface of the electrocardiographic signal processing circuit unit 3 in the storage case 1. Therefore, even if the electrocardiographic signal processing circuit unit 3 in the storage case 1 can be rotationally arranged, regardless of the rotational position, the two detecting electrodes 5 are always connected to the two electrodes 3a on the one diagonal line on the lower surface thereof, while the four indifferent electrodes 6 are always connected to the two electrodes 3a on the other diagonal line on the lower surface thereof, thereby preventing erroneous connection of the electrodes. As will be appreciated from the above, the electrode 3a on the lower surface of the electrocardiographic signal processing circuit unit 3, to which the indifferent electrode 6 is connected, may be only one of the above two electrodes 3a on the other diagonal line. Further, it is desirable that the connecting parts 7 and the electrodes 3a are positioned at the four corners of the square.

Figure 8:
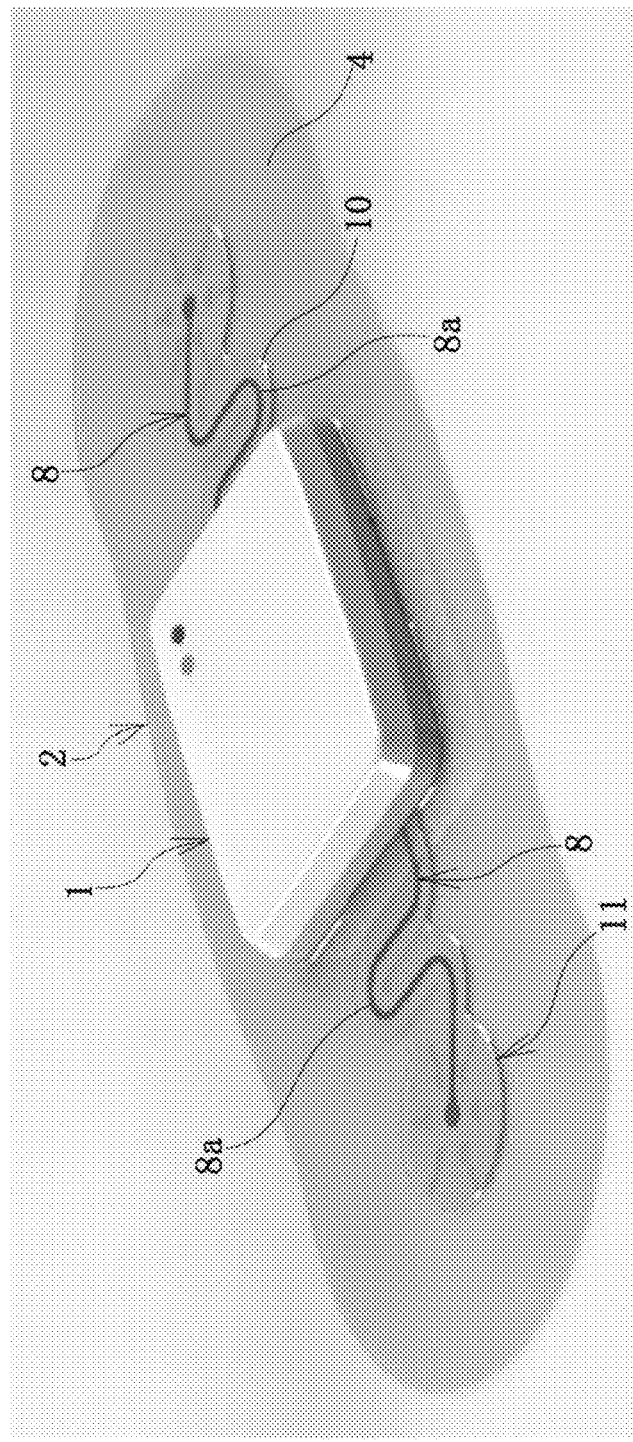
FIG. 8 is a perspective view showing a storage case with a biomedical electrode pad according to another practical embodiment of the present invention and a Holter electrocardiograph including the storage case of the said practical embodiment, which are viewed from a front surface side of the biomedical electrode pad.
Figure 9:
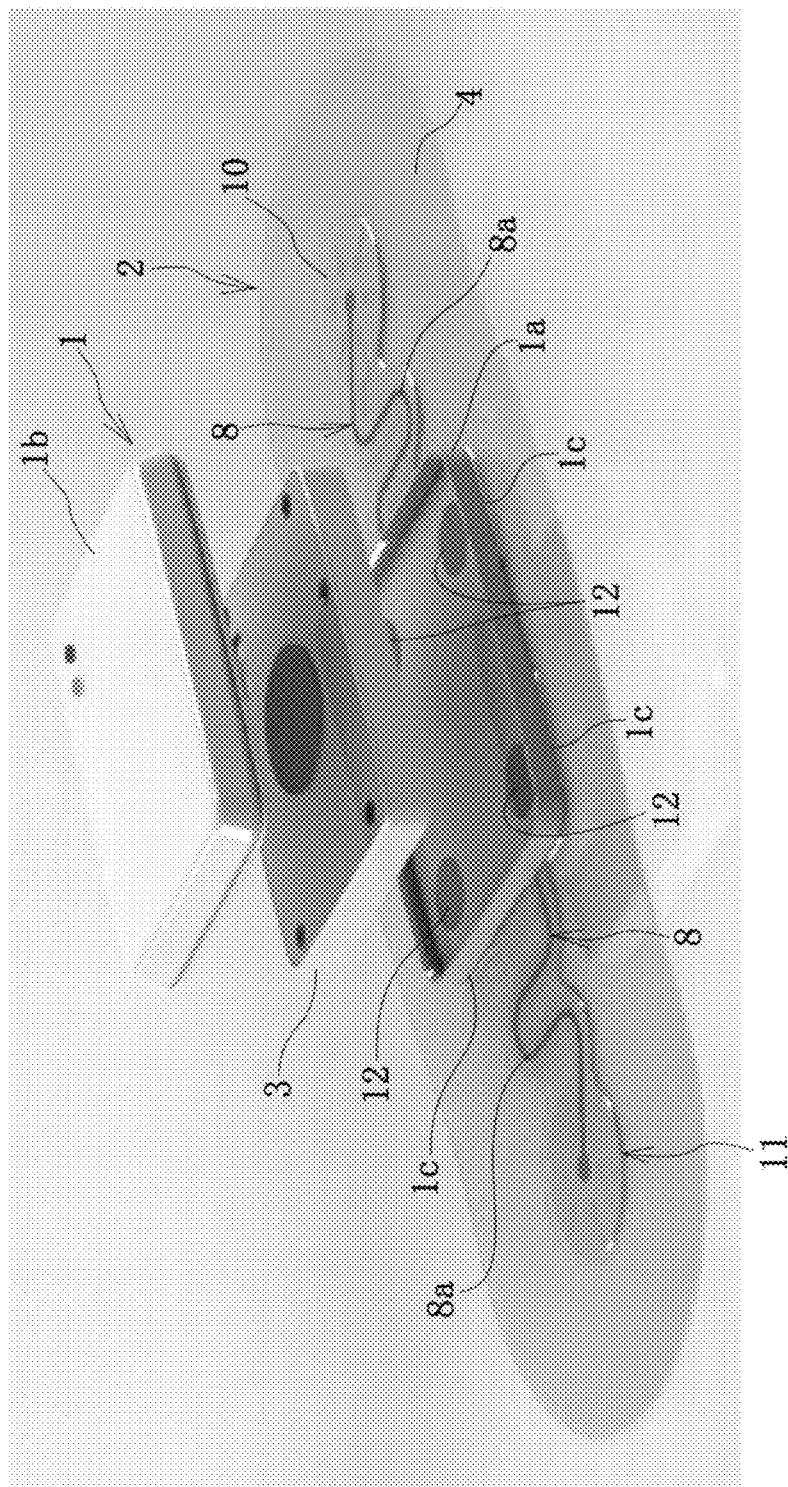
FIG. 9 is an exploded perspective view showing the storage case with the biomedical electrode pad of the said practical embodiment and the Holter electrocardiograph including the storage case of the said practical embodiment, which are viewed from the front surface side of the biomedical electrode pad.
Figure 10:
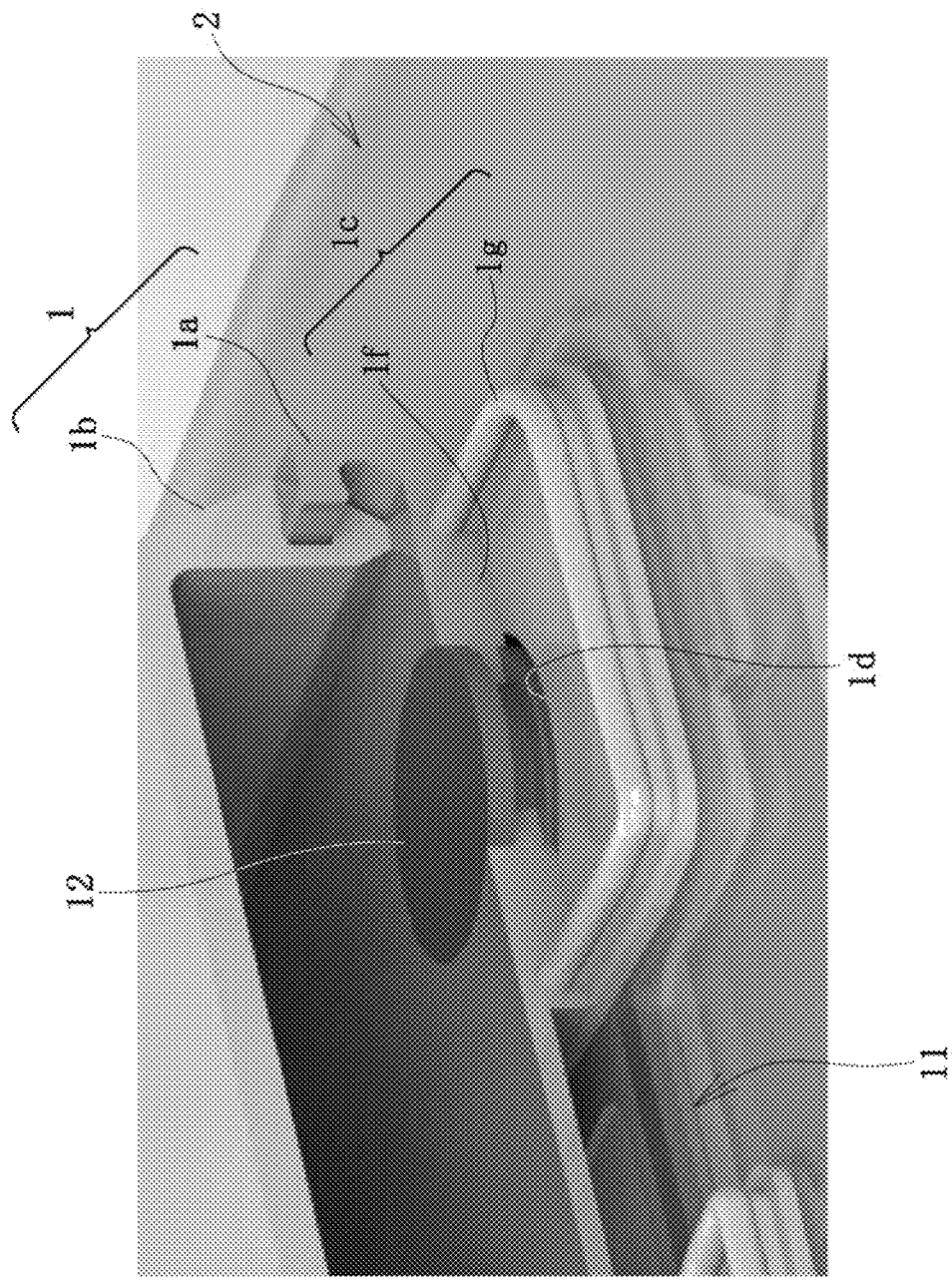
FIG. 10 is a perspective view showing the storage case with the biomedical electrode pad of the said practical embodiment by cutting out a part thereof, which is viewed from the front surface side of the biomedical electrode pad.
Figure 11:
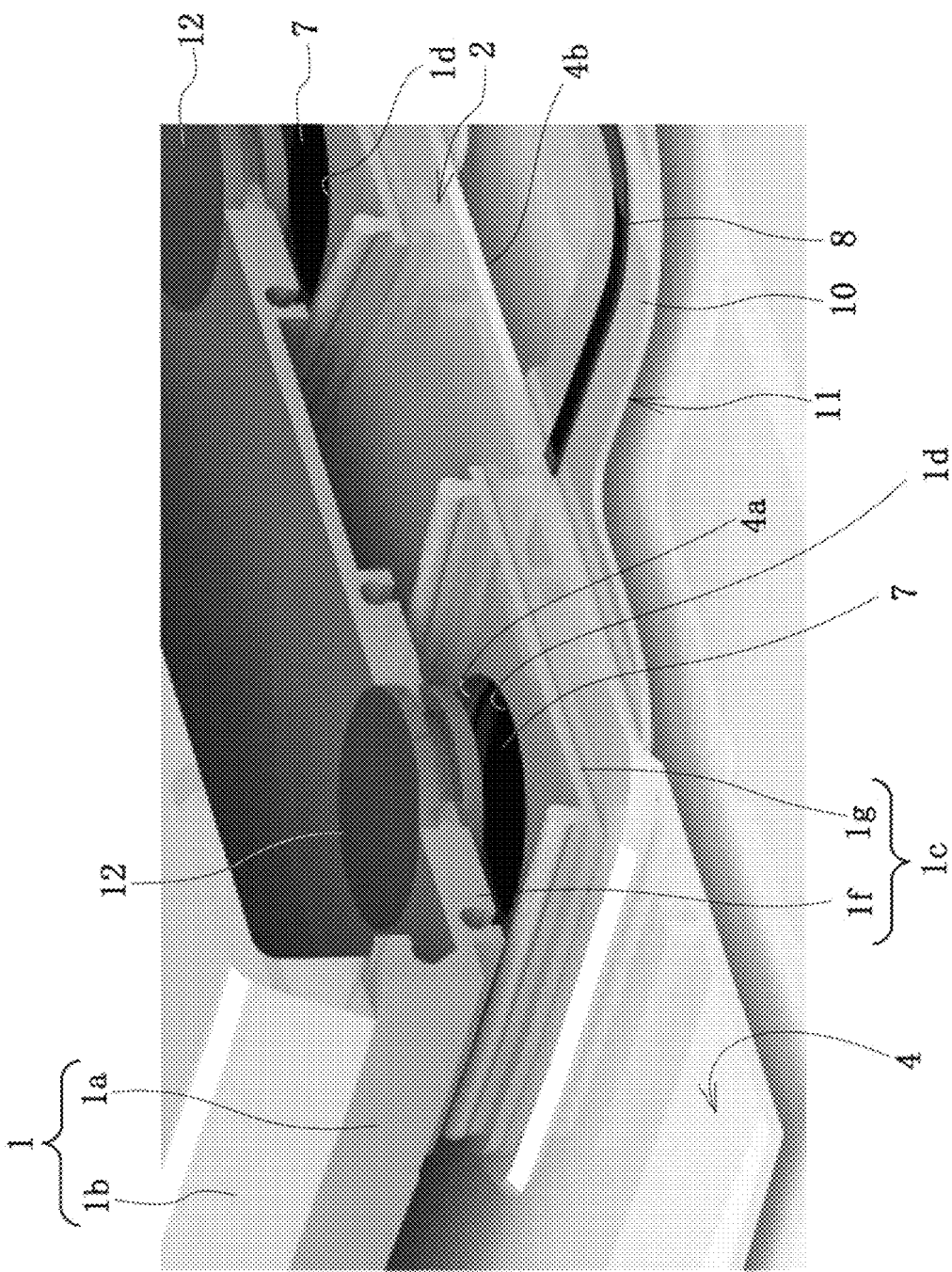
FIG. 11 is a perspective view showing the storage case with the biomedical electrode pad of the said practical embodiment by cutting out a part thereof, with the biomedical electrode pad detached from the storage case, which is viewed from the front surface side of the biomedical electrode pad.

FIG. 8 is a perspective view showing a storage case with a biomedical electrode pad according to another practical embodiment of the present invention and a Holter electrocardiograph including the storage case of the said practical embodiment, which are viewed from a front surface side of the biomedical electrode pad. FIG. 9 is an exploded perspective view showing the storage case with the biomedical electrode pad of the said practical embodiment and the Holter electrocardiograph including the storage case of the said practical embodiment, which are viewed from the front surface side of the biomedical electrode pad. FIG. 10 is a perspective view showing the storage case with the biomedical electrode pad of the said practical embodiment by cutting out a part thereof, which is viewed from the front surface side of the biomedical electrode pad. FIG. 11 is a perspective view showing the storage case with the biomedical electrode pad of the said practical embodiment by cutting out a part thereof, with the biomedical electrode pad detached from the storage case, which is viewed from the front surface side of the biomedical electrode pad. In FIG. 10, only the storage case 1 side is cut out to form a cross section, and in FIG. 11, both the attachment sheet 4 side and the storage case 1 side are cut out to form a cross section.

The storage case with the biomedical electrode pad of this practical embodiment and the Holter electrocardiograph of this practical embodiment using the same are different from those of the preceding practical embodiment mainly in configuration of the leg parts 1c of the receptacle case 1a. Thus, the said differences will be mainly explained here. In the drawings, the same parts as in the preceding practical embodiment are indicated by the same reference numerals.

That is, in the storage case 1 with the biomedical electrode pad of this practical embodiment, as shown in FIGS. 8 and 9, the receptacle case 1a is mounted on the approximately central part of on the front surface side of the attachment sheet 4 of the biomedical electrode pad 2. In the receptacle case 1a, a plurality of, that is, the four leg parts 1c in the illustrated example are each watertightly fixed to the attachment sheet 4. Further, between the leg parts 1c, a gap is formed so as to partially spread between the opposed faces of the front surface of the attachment sheet 4 and the receptacle case 1a and is open to the external space through the adjacent leg parts 1c. Moreover, the storage case 1 with the biomedical electrode pad of the present practical embodiment includes the cover case 1b which is watertightly and detachably fitted to the receptacle case 1a to form the storage case. Besides, as shown in FIGS. 10 and 11, the storage case 1 with the biomedical electrode pad of the present practical embodiment also includes four elastic connecting members 12 that are located within the respective openings 1d of the leg parts 1c of the receptacle case 1a and the respective openings 4a of the central part of the attachment sheet 4 so as to penetrate therethrough. Similarly to the preceding practical embodiment, the four elastic connecting members 12 are elastically in contact with the four connecting parts 7 exposed from the respective four openings 4a in the central part of the attachment sheet 4 to the front surface side of the attachment sheet 4 and with the four electrodes 3a on the lower surface of the electrocardiographic signal processing circuit unit 3 in the storage case 1, so as to electrically connect the each pair of the connecting part 7 and the electrodes 3a.

However, the four leg parts 1c of the receptacle case 1a in this practical embodiment are each attached to the attachment sheet 4 with a special fitting and fixing structure. Specifically, the fitting and fixing structure is shown in the fitted state in FIG. 10 and in the separated state in FIG. 11.

That is, the fitting and fixing structure includes a proximal part 1f integrally formed with the receptacle case 1a and a distal end part 1g fixed to the front surface of the central part of the attachment sheet 4.

The distal end part 1g has a sheet-like base part that is overlapped in close contact and fixed to the front surface of the attachment sheet 4, and the upper surface of the connecting part 7 is exposed through a penetration hole provided in the center of the base part. Further, near the outer peripheral edge of the base part, an engaging projection projecting toward the upper surface side (the storage case 1 side) is continuously formed in an annular shape over the entire circumference so as to form an annular convex part.

Meanwhile, the proximal part 1f is configured by utilizing the leg part 1c projecting downward (toward the attachment sheet 4 side) from the bottom wall of the receptacle case 1a. That is, near the outer peripheral edge of the projecting distal end surface of the leg part 1c, an engaging groove that opens downward is formed in an annular shape continuously over the entire circumference so as to form an annular concave part. Further, the portion of the proximal part 1f surrounded by the annular concave part projects toward the attachment sheet 4 side, and is configured to be attached so as to enter the region surrounded by the annular convex part of the distal end part 1g on the attachment sheet 4 side. Besides, the opening 1d formed in the leg part 1c penetrates through the central portion of the proximal part 1f, and the lower surface of the elastic connecting member 12 attached to the opening 1d is exposed in a projecting state to the lower surface (the projecting distal end surface) of the proximal part 1f.

In short, the annular concave part of the proximal part 1f is formed at a position corresponding to the annular convex part of the distal end part 1g on the attachment sheet 4 side. Further, an engaging head part of generally spherical shape is formed at the distal end of the annular convex part of the distal end part 1g over the entire circumference in the circumferential direction, while a corresponding engaging bottom part of generally spherical shape is formed at the bottom of the annular concave part of the proximal part 1f over the entire circumference in the circumferential direction. By the proximal part 1f being fitted into the distal end part 1g, the engaging head part is engaged with or locked to the engaging bottom part.

With this configuration, regarding the proximal part 1f integrally formed with the receptacle case 1a and the distal end part 1g fixed to the front surface of the central part of the attachment sheet 4, the annular concave part of the proximal part 1f and the annular convex part of the distal end part 1g are fitted to each other, so that the proximal part 1f and the distal end part 1g are detachably and watertightly fitted to each other. Then, within the opening 1d penetrating the proximal part 1f and the distal end part 1g, the elastic connecting member 12 is located so as to penetrate therethrough, and the connecting part 7 is conductive with respect to the elastic connecting member 12 in a contact state.

The other configurations of the storage case 1 with the biomedical electrode pad of this practical embodiment are similar to those in the preceding practical embodiment except that the meandering direction of the stretchable portion 8a of the detecting electrode connecting wiring 8 is opposite to that of the preceding practical embodiment.

Therefore, according to the storage case 1 with the biomedical electrode pad of this practical embodiment and the Holter electrocardiograph of this practical embodiment using the same, similar working effects to those in the storage case 1 with the biomedical electrode pad and the Holter electrocardiograph of the preceding practical embodiment can be achieved. In addition, the receptacle case 1a and the biomedical electrode pad 2 can be easily separated between the proximal part 1f and the distal end part 1g of the leg part 1c, so that only one of them can be sterilized and cleaned, or replaced when damaged as necessary.

Although descriptions are given based on the illustrated examples, the present invention is not limited to the above-described examples and can be appropriately modified within the scope of the claims. For example, in the biomedical electrode pad of the present invention, the number, arrangement, shape, etc. of the electrodes can be appropriately changed according to the measurement target, application, and the like. Specifically, for example, the indifferent electrodes 6 may be omitted and the number of the detecting electrodes 5 may be three or more. In that case, the indifferent electrode 6 at the central part may be changed to the detecting electrode 5. Further, the plurality of electrodes need not be arranged side by side in the same direction.

Moreover, the biomedical electrode pad of the storage case with the biomedical electrode pad of the present invention can be used for detection of a myoelectric signal in place of or in addition to the detection of the electrocardiographic signal. Besides, the biological signal processing circuit unit and the biological signal processing device of the present invention stored in the storage case with the biomedical electrode pad of the present invention may record and output a myoelectric signal in place of or in addition to the electrocardiographic signal.

Additionally, in the present invention, regarding the power supply that supplies power to the electrocardiographic signal processing circuit unit 3, for example, a battery may be irreplaceably or replaceably attached to the substrate of the electrocardiographic signal processing circuit unit 3. Alternatively, the power supply may be stored in the storage case separately from the electrocardiographic signal processing circuit unit 3, or may be equipped by being stored separately from the storage case of the electrocardiographic signal processing circuit unit 3, preferably by being sealed in a watertight case.

Further, the electrocardiographic signal processing circuit unit 3 may be a device that only directly outputs the detection signal by the biomedical electrode pad 2 to the outside wirelessly or by wire. It would also be possible to store the detection signal to an external storage device different from the electrocardiographic signal processing circuit unit 3.

Besides, various wirings connected to the electrodes can be provided on either the front surface or the back surface of the attachment sheet 4, and the specific wiring structure is not limited. For example, at least a part of the wiring can be configured by a lead or the like that is not fixed to the attachment sheet 4.

In addition, as is clear from the description of each preferred embodiment in the above-mentioned "MEANS FOR SOLVING THE PROBLEM" section, in some preferred embodiments of the present invention, the electrode connecting wiring having a stretchable portion and the case structure having watertightness, the conductive members inside and outside of the case using the elastic connecting member, the attachment sheet having water permeability, the gap between the attachment pad and the storage case (the case body), and the like are not essential for constituting the present invention unless described in each preferred embodiment. Further, as is clear from the description of each preferred embodiment in the above-mentioned "EFFECT OF THE INVENTION" section, the invention described in each preferred embodiment can exhibit effects such as improving the wearability or the wearing feeling of the storage case with the biomedical electrode pad and the biological signal processing device even without the configuration that is not described in each preferred embodiment.

Furthermore, the gap between the attachment pad and the storage case (the case body) may be opened to the external space through, for example, a groove, a hole, or a ventilation path provided in the case body, other than being directly opened to the external space as in the preceding practical embodiment.

Also, the structure of the storage case (the case body) for storing the biological signal processing circuit unit is not limited to the upper and lower two-part division structure as described above. For example, it would also be possible to allow the biological signal processing circuit unit having a generally plate shape to be stored by being inserted from the lateral side through the lateral opening that partially opens in the peripheral wall. When the upper and lower two-part division structure is adopted as in the preceding practical embodiment, there is an advantage that the electrical contact of the biological signal processing circuit unit can be stably held in the connected state with respect to the elastic connecting member exposed to the bottom surface of the receptacle case by the force of pressing the biological signal processing circuit unit from above by utilizing the locking and fixing force of the cover case to the receptacle case, or the like.

However, as described above, in the specific preferred embodiment of the present invention, such an elastic connecting member is not essential, and for example, the biological signal processing circuit unit may be fixedly mounted in the storage case. Further, the electrical contact by the elastic connecting member is not limited by the preceding practical embodiment. Various types of electrical contacts can be adopted, such as a structure in which, for example, a connector having a slit-shaped opening into which one end edge of the biological signal processing circuit unit is inserted is provided in the storage case, and an elastic contact (an elastic connecting member) provided in the slit-shaped opening is pressed against a contact exposed to the surface of the end edge of the substrate or the like of the biological signal processing circuit unit to be inserted into the opening, so as to be conductive.

In the practical embodiment of the storage case with the biomedical electrode pad shown in FIGS. 8 to 11, the entire storage case 1 (the case body) including the receptacle case 1a and the cover case 1b is attached to the attachment sheet 4 in a detachable manner. Then, it is possible to detach the electrocardiographic signal processing circuit unit 3 together with the storage case 1 with the electrocardiographic signal processing circuit unit 3 mounted in the storage case 1 in the stored state, or the entire storage case 1 from which the electrocardiographic signal processing circuit unit 3 is removed. This makes it possible to efficiently clean and sterilize the attachment sheet 4 and the storage case 1 in a single state, as well as to easily deal with repairs etc. such as replacing only one of them and reusing the other. Besides, the electrocardiographic signal processing circuit unit 3 can also be reused together with the storage case 1.

Thus, as can be understood from the preceding practical embodiment, in the storage case with the biomedical electrode pad according to some specific preferred embodiments (not all of them) of the present invention, the storage case with the biomedical electrode pad is attached to and detached from the biological signal processing circuit by the cover case being attached to and detached from the receptacle case, so that the storage case and the biomedical electrode pad can be easily sterilized and cleaned, or replaced when damaged. Moreover, even if the attachment sheet is expanded more than before to expand the range in which the biological signal can be detected, the detection of the biological signal from the skin by the plurality of electrodes can be sustained for a long period of time, regardless of the deformation of the limb due to body movement, thereby also improving the wearing feeling of the attachment sheet on the skin at that time.

Additionally, with the biological signal processing device using the storage case with the biomedical electrode pad according to some specific preferred embodiments (not all of them) of the present invention, the biological signal processing circuit unit is stored inside of the storage case in a watertight and detachable manner. Thus, while the above-described working effects of the storage case with the biomedical electrode pad are achieved, the biological signal processing circuit unit in the storage case is able to process the biological signal detected from the skin of the subject by the electrodes of the biomedical electrode pad, as well as to output the processing result by recording on a recording medium, by transmitting wirelessly, and the like.

INDUSTRIAL APPLICABILITY

The storage case with the biomedical electrode pad and the biological signal processing device including the storage case with the biomedical electrode pad, to which the present invention is applied, are industrially produced. Also, in use, they can be used in medical fields and non-medical fields (for example, physical fitness measurement, information processing and judgment of exercise intensity, living environment, and the like using data such as electrocardiographic waveform, heart rate, myoelectric waveform, etc.). Therefore, the present invention has industrial applicability.

KEYS TO SYMBOLS 1 storage case
1a receptacle case
1b cover case
1c leg part
1d opening
1e inside flange
1f proximal part
1g distal end part
2 biomedical electrode pad
3 electrocardiographic signal processing circuit unit
3a electrode
4 attachment sheet
4a opening
4b recess
4c adhesive surface
5 detecting electrode
6 indifferent electrode
7 connecting part
8 detecting electrode connecting wiring
8a stretchable portion
8b penetration part
9 indifferent electrode connecting wiring
9a penetration part
10 resin substrate
11 flexible wiring board
12 elastic connecting member
12a outer peripheral annular groove

The invention claimed is:

1. A storage case with a biomedical electrode pad attached, the biomedical electrode pad being configured to be attached to a skin of a living body and used to detect a biological electrical signal from the skin, the storage case with the biomedical electrode pad being configured to watertightly and detachably store a biological signal processing circuit unit inside, the biological signal processing circuit unit having a battery as a power source and processing the biological electrical signal detected by the biomedical electrode pad, wherein the biomedical electrode pad comprises:
an attachment sheet having water vapor permeability, the attachment sheet being elastically stretchable and having an electrically insulating property while including, on a back surface side, an adhesive surface suitable to be attached to the skin of the living body;
a plurality of electrodes located apart from one another on the back surface side of the attachment sheet and exposed to the back surface side;
a plurality of connecting parts that are located at a central part of the back surface side of the attachment sheet and covered with electrical insulation while being exposed to a front surface side through an opening of the attachment sheet; and
an electrode connecting wiring that is located on the back surface side of the attachment sheet and covered with electrical insulation while having a stretchable portion in at least a part of the electrode connecting wiring, and that electrically connects the plurality of electrodes with corresponding ones of the plurality of connecting parts, and the storage case comprises:
a receptacle case including a plurality of leg parts fixed to a central part of the front surface side of the attachment sheet of the biomedical electrode pad, and forming, between the leg parts, a gap partially between a front surface of the attachment sheet and the receptacle case;
a cover case that is watertightly and detachably fitted to the receptacle case; and an elastic connecting member penetrating through an opening in each of the leg parts of the receptacle case and through the opening at the central part of the attachment sheet to be located within the openings such that the elastic connecting member is elastically in contact with each of the plurality of connecting parts exposed from the opening at the central part of the attachment sheet to the front surface side of the attachment sheet and with the biological signal processing circuit unit in the storage case to electrically connect the each of the plurality of connecting parts and the biological signal processing circuit unit, wherein the plurality of leg parts of the receptacle case each include a proximal part fixed to the receptacle case and a distal end part detachably fitted to the proximal part while being fixed to the central part of the front surface side of the attachment sheet of the biomedical electrode pad.

2. The storage case with the biomedical electrode pad according to claim 1, wherein the plurality of electrodes include an indifferent electrode and a plurality of detecting electrodes.

3. The storage case with the biomedical electrode pad according to claim 1, wherein a flexible wiring board is constituted by: a resin substrate; the plurality of electrodes arranged on a lower surface of the resin substrate; the plurality of connecting parts arranged on an upper surface of the resin substrate; and the electrode connecting wiring arranged on the upper surface of the resin substrate, an end part of the electrode connecting wiring penetrating through the resin substrate to electrically connect the plurality of electrodes with corresponding ones of the plurality of connecting parts.

4. The storage case with the biomedical electrode pad according to claim 1, wherein at least one of the receptacle case and the cover case is made of a soft resin.

5. The storage case with the biomedical electrode pad according to claim 1, wherein the proximal part is formed in an annular shape so as to surround an entire circumference around the opening in each of the leg parts wherein the elastic connecting member is located, the distal end part is formed in an annular shape so as to surround an entire circumference around the opening at the central part of the attachment sheet wherein the elastic connecting member is located, and an annular concave part provided on one of the proximal part and the distal end part and an annular convex part provided on another of the proximal part and the distal end part are fitted to each other so that the proximal part and the distal end part are detachably and watertightly fitted to each other.

6. A biological signal processing device including the storage case with the biomedical electrode pad according to claim 1, wherein the biological signal processing circuit unit is stored inside the storage case with the biomedical electrode pad.

* * * * *